(12) United States Patent
Aldred

(10) Patent No.: US 10,786,411 B2
(45) Date of Patent: Sep. 29, 2020

(54) REALIGNMENT OF THE PELVIS

(71) Applicant: PELVIPRO LIMITED, North Yorkshire (GB)

(72) Inventor: Chris David Aldred, North Yorkshire (GB)

(73) Assignee: PELVIPRO LIMITED, North Yorkshire (GB)

( * ) Notice: Subject to any disclaimer, the term of this patent is extended or adjusted under 35 U.S.C. 154(b) by 250 days.

(21) Appl. No.: 15/563,914

(22) PCT Filed: Apr. 11, 2016

(86) PCT No.: PCT/GB2016/000079
§ 371 (c)(1),
(2) Date: Oct. 2, 2017

(87) PCT Pub. No.: WO2016/162655
PCT Pub. Date: Oct. 13, 2016

(65) Prior Publication Data
US 2018/0116894 A1 May 3, 2018

(30) Foreign Application Priority Data
Apr. 9, 2015 (GB) .................................. 1506061.9

(51) Int. Cl.
*A61H 1/00* (2006.01)
*A61B 17/64* (2006.01)
*A61B 5/00* (2006.01)

(52) U.S. Cl.
CPC ......... *A61H 1/008* (2013.01); *A61B 17/6433* (2013.01); *A61B 5/4504* (2013.01); *A61H 2201/1623* (2013.01); *A61H 2201/1628* (2013.01); *A61H 2201/1676* (2013.01); *A61H 2203/0456* (2013.01)

(58) Field of Classification Search
CPC .......... A61H 1/02; A61H 1/006; A61H 1/008; A61H 1/024; A61H 1/0244; A61H 1/0237; A61H 1/0255; A61H 1/0292; A61H 2201/0153; A61H 2201/0157; A61H 2201/1623; A61H 2201/1628; A61H 2201/1657; A61H 2201/1676; A61H 2201/1666; A61H 2201/1671; A61H 2201/1673; A61H 2205/088;
(Continued)

(56) References Cited

U.S. PATENT DOCUMENTS 2,554,337 A * 5/1951 Lampert ................. A61F 5/028
606/237
3,620,210 A * 11/1971 Annas ....................... A61H 1/02
606/245
(Continued)

FOREIGN PATENT DOCUMENTS

EP          3485863 A1 *  5/2019   ....... A63B 21/00178

*Primary Examiner* — Kendra D Carter
*Assistant Examiner* — Paige Kathleen Bugg
(74) *Attorney, Agent, or Firm* — Edwin D. Schindler

(57) ABSTRACT

A device for assisting the realignment of the pelvis comprises a pair of arms (3,5) connected together at one end of each arm by a connection member (7) allowing relative rotation of the two arms in a plane passing through the longitudinal axes of both arms and also about an axis passing through the connected ends of the arms. A method of using such a device is disclosed.

12 Claims, 4 Drawing Sheets

(58) Field of Classification Search
CPC ...... A61H 2203/0456; A61H 2203/102; A61H 2203/108; A61B 17/6433; A61B 5/4504
USPC .......................... 606/237, 241, 245; 601/18
See application file for complete search history.

(56) References Cited

U.S. PATENT DOCUMENTS

| | | | | |
|---|---|---|---|---|
| 3,661,149 A * | 5/1972 | Ferries | ................. | A61H 1/0237 601/35 |
| 4,076,237 A * | 2/1978 | Dussia | ................. | A61H 1/0292 482/121 |
| 4,566,440 A * | 1/1986 | Berner | ................. | A61H 1/0255 601/34 |
| 5,122,106 A * | 6/1992 | Atwood | ............... | A61H 1/0244 482/131 |
| 5,280,783 A * | 1/1994 | Focht | .................. | A61H 1/0259 601/34 |
| 5,406,942 A * | 4/1995 | Loo | .......................... | A61F 5/028 128/100.1 |
| 5,733,291 A * | 3/1998 | Guidera | .................... | A61F 5/04 606/105 |
| 6,971,392 B2 * | 12/2005 | Lindahn | ................. | A61H 1/024 128/845 |
| 7,153,251 B2 * | 12/2006 | Broadbent | ........... | A61H 1/0237 482/148 |
| 7,246,390 B2 * | 7/2007 | Mitsuishi | ............. | A61H 1/0237 5/621 |
| 7,744,552 B1 * | 6/2010 | Babcock | ................. | A61F 5/026 602/19 |
| 9,717,640 B1 * | 8/2017 | Pleasants | ............. | A61H 1/0292 |
| 2001/0007845 A1 * | 7/2001 | Afanasenko | ....... | A63B 21/0004 482/124 |
| 2003/0230310 A1 * | 12/2003 | Day | .......................... | A61F 5/01 128/845 |
| 2005/0096700 A1 * | 5/2005 | Tanaka | .................. | A61F 5/0193 606/237 |
| 2009/0054816 A1 * | 2/2009 | Zake | ..................... | A61H 7/001 601/135 |
| 2009/0093743 A1 * | 4/2009 | Corzine | ................ | A61H 7/003 601/136 |
| 2009/0198276 A1 * | 8/2009 | Lee | .......................... | A61F 5/01 606/237 |
| 2011/0224585 A1 * | 9/2011 | Hall | ...................... | A61H 1/008 601/34 |
| 2011/0278866 A1 * | 11/2011 | Lee | ...................... | E05C 19/004 292/339 |
| 2012/0006335 A1 * | 1/2012 | Lee | ..................... | A61H 1/0244 128/845 |
| 2012/0046578 A1 * | 2/2012 | Agrawal | ............... | A61H 3/008 601/35 |
| 2012/0258842 A1 * | 10/2012 | Davidow | ......... | A63B 21/00047 482/91 |
| 2013/0237886 A1 * | 9/2013 | Gavoni | .................. | A61H 7/001 601/83 |
| 2016/0045355 A1 * | 2/2016 | Safko | ..................... | A61F 5/028 602/19 |

* cited by examiner

REALIGNMENT OF THE PELVIS

CROSS-REFERENCE TO RELATED PATENT APPLICATIONS

This application is a U.S. National Phase Application under 35 U.S.C. § 371 of International Patent Application No. PCT/GB2016/000079, filed Apr. 11, 2016, and claims the priority of GB 1506061.9, filed Apr. 9, 2015, all of which are incorporated by reference in their entireties. The International Application was published on Oct. 13, 2016 as International Publication No. WO 2016/162655 A1.

FIELD OF INVENTION

The invention relates to devices and methods for the treatment of lower back pain and problems associated therewith.

BACKGROUND OF THE INVENTION

A major cause of lower back and pelvic pain is the misalignment of joints in and around the spine and pelvis, these joints being the lumbar facet joints L5/S1 facet joints, the sacroiliac joints, the pubic symphysis and the hip joints.

U.S. Pat. No. 6,971,392 discloses a device for localised bone mobilization in the pelvic area. The device comprises a base member having fixed arms oriented in a horizontal plane at an angle of approximately 45° to one another. One end of the base member serves as a handle and may be tapered for ease of holding. Affixed at the opposite end of the base member is a short rod and affixed at the intersection of the two fixed arms is a long rod extending in the same direction as the short rod. Both rods are attached substantially perpendicular to the base member.

In use the device enables an individual to generate a lateral and caudal directed force on an affected ilium thereby mobilizing it back into its normal position.

JP4,769,327 discloses a cushion having a seat portion, a sacrum contact tool which contacts the sacrum or coccyx and an ilium contact portion which contacts the ilium. When an individual is seated on the cushion, a sacrum raising moment acts on the sacrum and an ilium forward-tilting moment acts on the ilium. The posture of the pelvis is corrected by the effect of these moments.

STATEMENTS OF THE INVENTION

According to the present invention, there is provided a device for assisting the realignment of the pelvis comprising a pair of arms connected together at one end of each arm by a connection member allowing relative rotation of the two arms in a plane passing through the longitudinal axes of both arms and also about an axis passing through the connected ends of the arms.

Preferably, one of said arms has a width which decreases, over at least a portion of its length, in a direction towards the other arm. More preferably, said one arm is substantially triangular in cross-section.

Preferably, said connection member has a first part connected to said one arm and a second part rotatably connected to said first part, said other arm being pivotably connected to said second part.

Preferably, said connection member is substantially spherical. More preferably, said connection member is provided with a cut-out portion which accommodates an end of said one arm.

Preferably, one of said arms is profiled to provide an upper protuberance enabling the member to be firmly gripped.

Preferably, one of said arms is provided with a recessed surface located on that side of the arm remote from the other arm. Preferably this arm is provided with rubber footings.

The present invention also provides a method of using the device of the invention, the method comprising adopting a supine position on a support surface such as a floor, locating one arm of the device underneath the sacrum and positioning the other arm of the device on top of the ASIS on that side to be realigned, flexing the hip and the knee, exerting a downward force on the other arm and extending the hip and the knee until the heel is positioned at or close to the support surface.

The realignment of the joints in and around the pelvis in turn repositions ligaments. Ligaments join bone to other bones. The main groups of ligaments that are repositioned and are therefore less likely to form pathological injury are directly the sacral ligaments and indirectly the spinal and hip ligaments as an effect of the resulting pelvic reorientation.

The realignment of the joints returns muscles back to their correct position and therefore to their correct roles. When out of position muscles can be in a state of inhibition and cease functioning and performing the role they exist to perform, in which case other muscles have to compensate to allow a biomechanical function to take place. The pelvis muscle groups involved are the core, abdominal, paraspinal, pelvic floor and hip muscles.

DETAILED DESCRIPTION OF THE INVENTION

Figure 1:
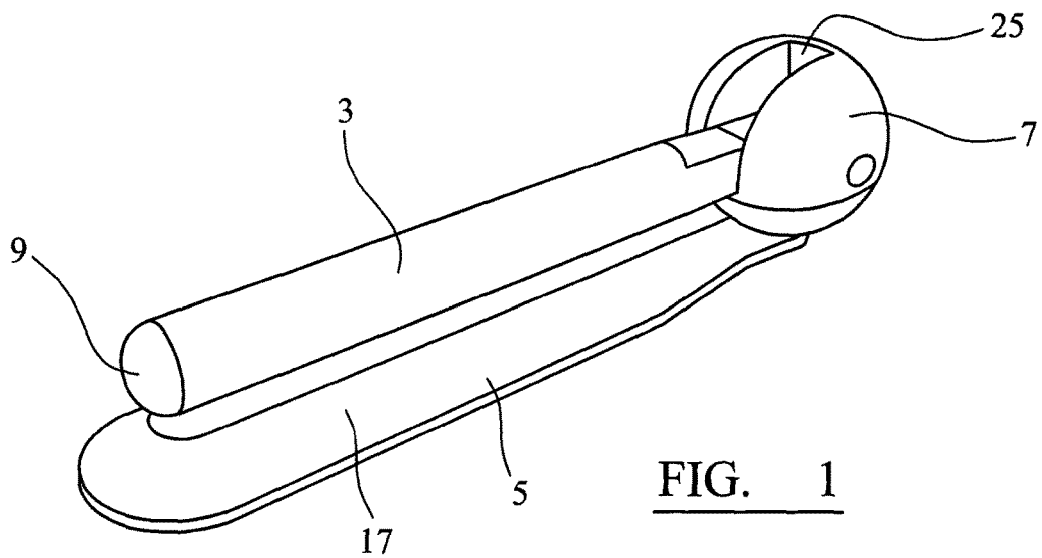
FIG. 1 is a perspective view of a device of the invention.

The invention will now be described, by way of example only, with reference to the accompanying drawings.

Referring to FIGS. 1 to 4 of the accompanying drawings, a device 1 for realignment of the pelvis comprises two arms, handle arm 3 and base arm 5, connected together at one end of each arm by means of a substantially spherical connection member 7. As shown in the drawings, the arms lie adjacent each other with upper arm 3 superimposed on lower arm 5. However, the connection member 7 allows relative movement of the arms both in the plane of the paper in FIG. 2 and in the plane of the paper in FIG. 3. These movements are possible due to the nature of the connection member 7 and the manner of the affixing of the ends of arms 3,5 to this member as will be described below Arm 3 is of circular cross-section along most of its entire length although with a rounded free end 9 and with its other end tapering at 11 to provide a smaller diameter end portion 13.

Arm 5 has a base portion 15 from which extends upwardly towards arm 3 a portion 17 having a width which decreases in a direction towards the other arm. More specifically, portion 17 is substantially triangular in cross-section although having a somewhat rounded apex. The free end of arm 5 is tapered as indicated at 19. The other end of arm 5 is affixed to a lower portion 21 of connection member 7.

Figure 2:
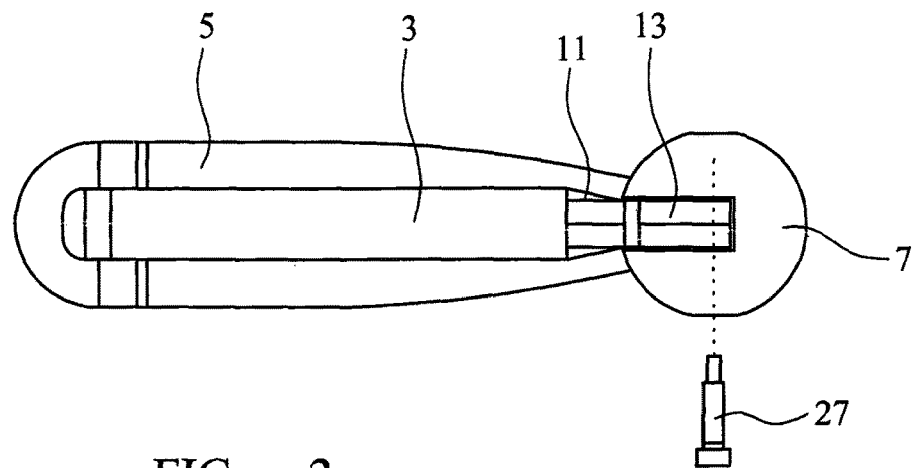
FIG. 2 is a top plan view of the device of FIG. 1.
Figure 3:
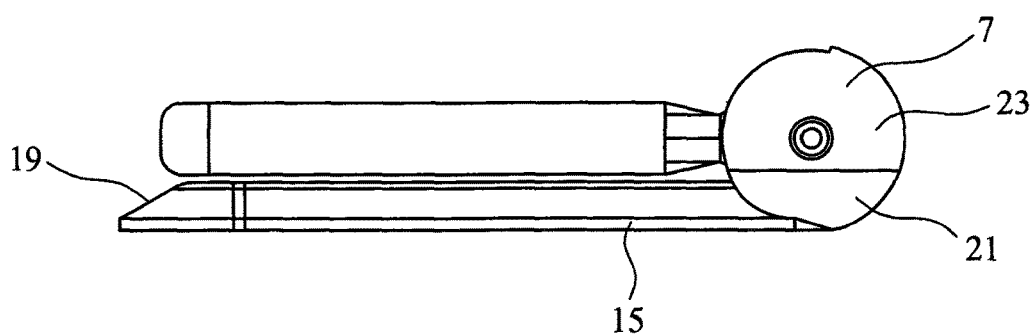
FIG. 3 is a side elevation of the device of FIG. 1.
Figure 4:
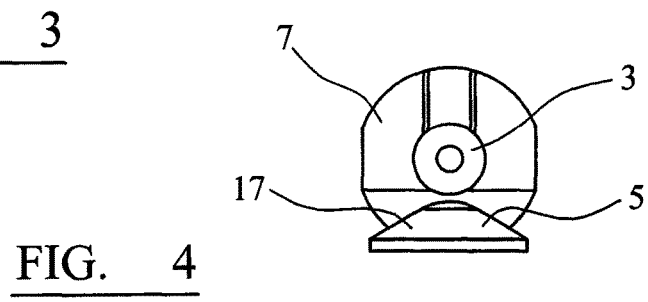
FIG. 4 is a front elevation of the device of FIG. 1.

Lower portion 21 of connection member 7 is connected to a larger upper portion 23 for relative rotation there between about an axis passing vertically through the centre of member 21 as viewed in FIG. 2. This allows the arms relatively to rotate in the plane of the paper in FIG. 2.

Connection member 7 is provided with a cut-out 25 which extends over a quarter of a circumference to just beyond the centre of the member and which has a width sufficient to accommodate end portion 13 of arm 3. Mounted within connection member 7 is a screw 27 which extends into the cut-out 25 and into end portion 13, allowing rotation of arm 13 thereabout.

The above described device may be used without assistance by a person seeking to realign his/her pelvis. The person lies supine (flat on the back) and slides the lower arm underneath the sacrum. This position is located by measuring four fingers down from the anterior superior iliac spine (ASIS) (the foremost prominent bony landmark that can be palpated on the body) in a direction towards the feet, tracking this level underneath the body—this lines up with the top of the lower arm.

The upper arm is then laid on top of the ASIS on the side to be corrected. The hip is flexed, on the side being corrected, to 90 degrees and the knee is also flexed to 90 degrees. A downward force is exerted on the upper arm in order to hold the ASIS steady.

The hip and knee are then smoothly extended with a moderate velocity so that the heel finishes a few centimeters from the floor. This causes the sacrum to nutate while the innominate bone, and thus the ilium, is held stable, thereby achieving "form closure." (Form closure is where the ilium and the sacrum are in their most stable proximity to one and other.) This action is repeated ten times. The same procedure is then carried out on the opposite side. There can only be movement of the joint if before the procedure is carried out, one or both of the joints are already in a state of "non-form closure." A joint that already has "form closure" will simply not move and no effect takes place at the sacroiliac joints.

Exercises are used to activate the appropriate muscles to hold the pelvis in its correct position since otherwise it is likely to misalign again. Some highly effective exercises require the position of a ball between either the knees or the ankles. The spherical connection member at the end of the above-described device may be used for this purpose.

Figure 5:
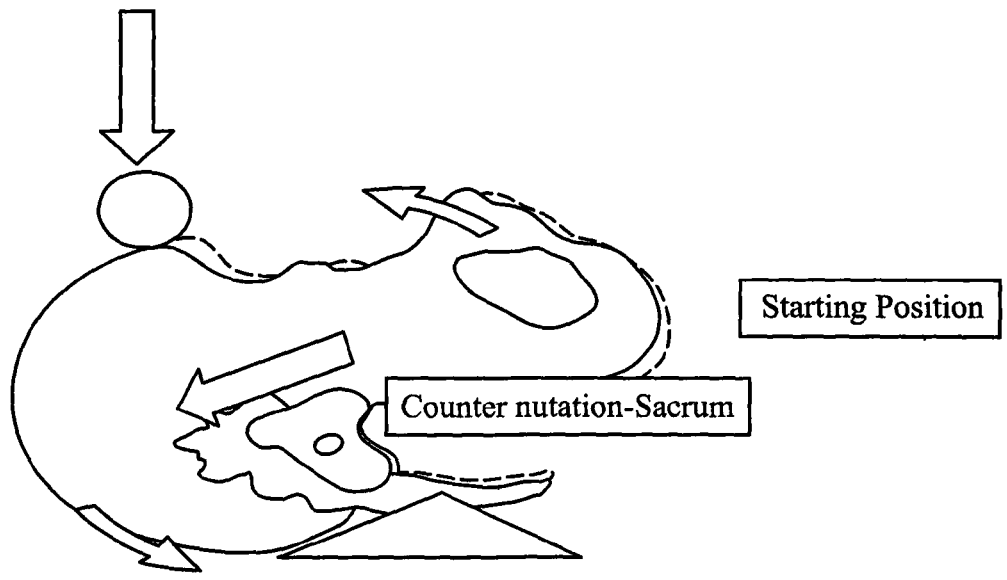
FIG. 5 illustrates a device of the invention in use and showing the starting and finishing positions.
Figure 5:
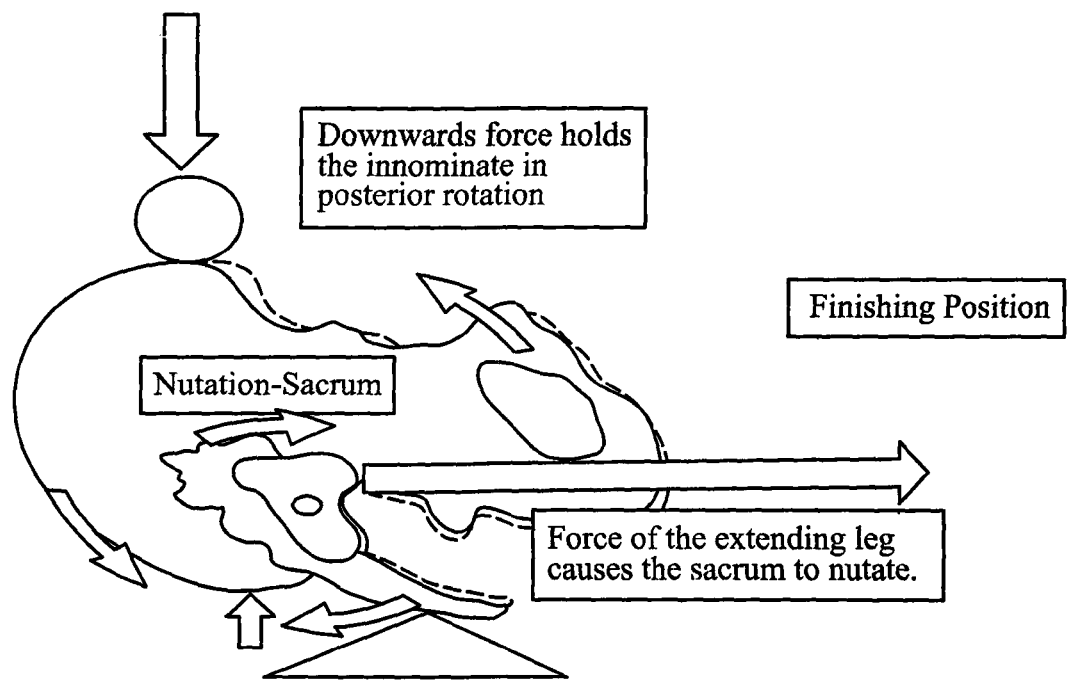
Figure 6:
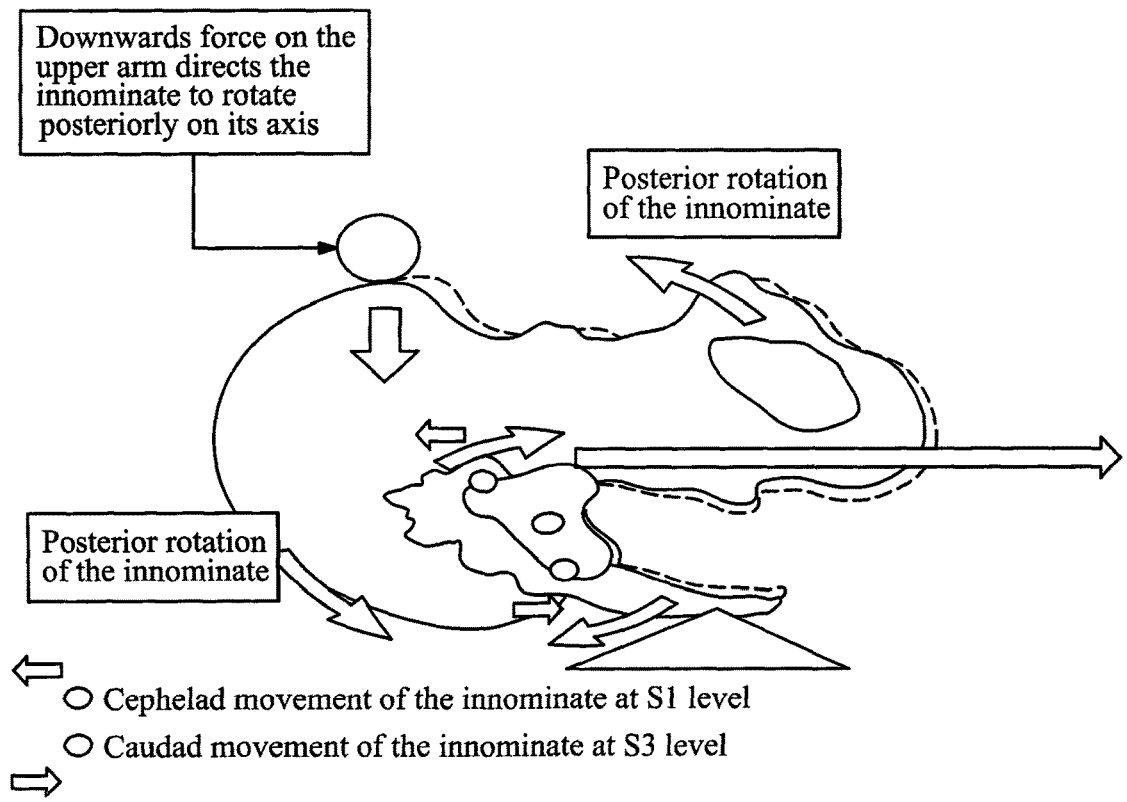
FIG. 6 is similar to the finishing position in FIG. 5 and giving further detail.

The above described device is effective in assisting the realignment of the pelvic innominate achieving Form Closer (Non-Form closer is when the pelvic innominate subluxes caudad at S1 and cephalad at S3). The device reverses for use on either side of the body and the lower arm has a gradient that holds pelvis in a posterior rotated starting position as the leg extends it shifts the whole pelvis into a anterior rotation and extention of the lumbar spine causing the sacrum to nutate as illustrated in FIG. 5. The upper arm holds —the innominate posteriorly on the sacrum, moving the articulating aspect of the innominate at the S1 level caudad in direction and the cephalad at S3 on the articulating aspect of the innominate, as illustrated in FIG. 6.

Figure 7:
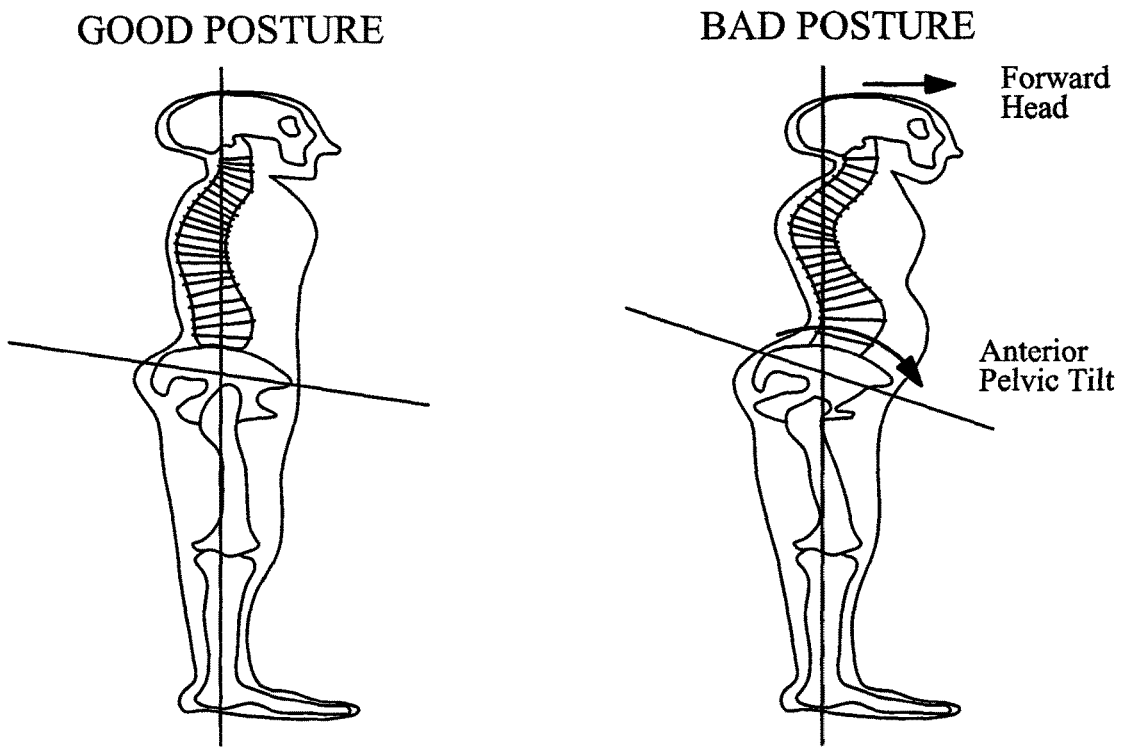
FIG. 7 illustrates good and bad postures.

The above described device orientates the pelvis into a "good posture" by taking the innominate out of the anterior tilted position, as illustrated in FIG. 7. The reorientation of the acetabulum over the femur also repositions the pelvis into a neutral position over the hip joints.

The four physiological tests which are used and which are positively affected by the use of the above described device are tool are the Gillets test, the leg length test, the adduction drop test and the adduction lift test.

Biomechanical benefits resulting from use of the above described device include: pelvic reorientation; mobilisation of L5/S1, sacroiliac joints, pubic synthesis and hip joints; re-establishment of ligament position and thus stability which reduces the risk of pathological injury; re-establishment of muscle position and thus synchronisation which also reduces the risk of pathological injury; and re-establishment of muscle synchronisation to improve biomechanical performance in normal everyday movements and in sport.

Figure 8:
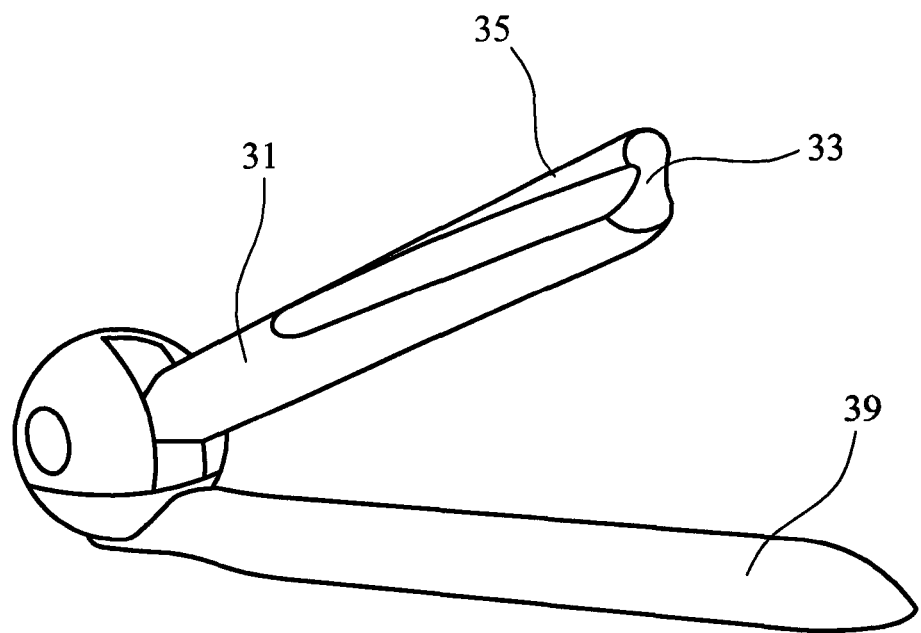
FIG. 8 is a perspective view a further device of the invention.
Figure 9:
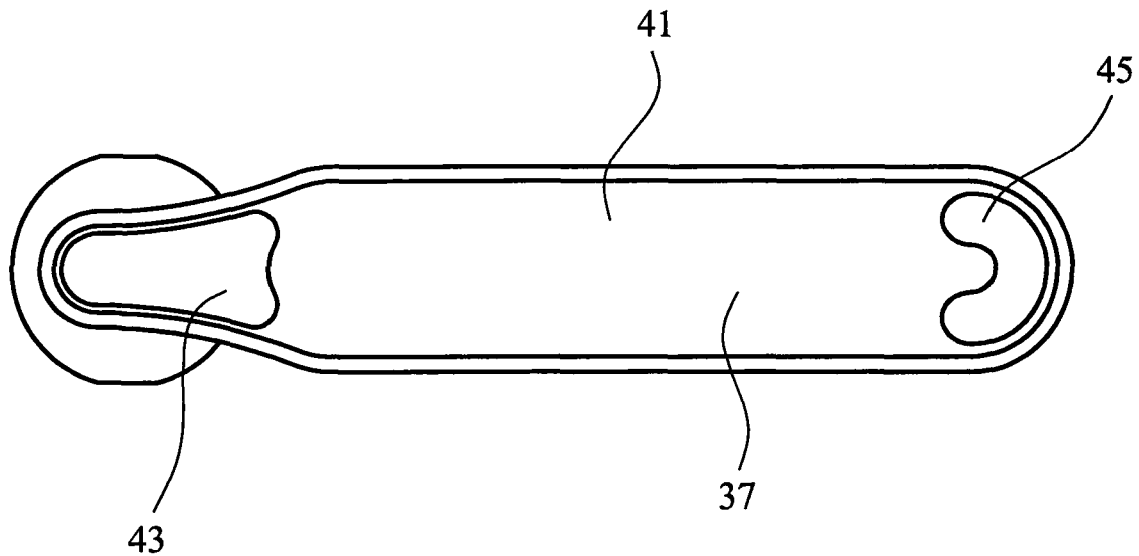
FIG. 9 is an underneath view of the device of FIG. 8.

Referring to FIGS. 8 and 9 of the accompanying drawings, another embodiment of a device of the invention is broadly similar to that described above. However, in this case the upper arm 31 is profiled over a portion extending to its free end 33 so that it has a gradually enlarging upper protubance 35 enabling the arm to be more easily and firmly gripped when holding this arm against the body.

The underneath of base portion 37 of arm 39 is provided with a concave longitudinal recess 41 and rubber footings 43 and 45 to give a good grip on a carpeted or wood floor.

The invention claimed is:

1. A method for utilizing an apparatus for assisting realignment of a pelvis of a person, said apparatus comprising:
a first arm and a second arm connected together at a connecting end of each of said first arm and said second arm via a connection member allowing for relative rotation of said first arm and said second arm in a plane passing through a longitudinal axis of each of said first arm and said second arm, and about an axis passing through said connecting end of each of said first arm and said second arm,
said method for utilizing said apparatus for assisting alignment of the pelvis of a person comprising the steps of:
adopting a supine position on a support surface;
locating said first arm of said apparatus underneath a person's sacrum;
positioning said second arm of said apparatus on top of the person's anterior superior iliac spine on a side of the person to be realigned;
flexing a hip and a knee of the person;
exerting a downward force on said second arm; and,
extending the hip and the knee of the person until a heel of the person is positioned at, or close to, the support surface.

2. The method for utilizing an apparatus for assisting realignment of a pelvis of a person according to claim 1, wherein said first arm has a width which decreases, over at least a portion of its length, in a direction towards said second arm.

3. The method for utilizing an apparatus for assisting realignment of a pelvis of a person according to claim 1, wherein said second arm has a width which decreases, over at least a portion of its length, in a direction towards said first arm.

4. The method for utilizing an apparatus for assisting realignment of a pelvis of a person according to claim 1, wherein at least one of said first arm and said second arm is substantially triangular in cross-section.

5. The method for utilizing an apparatus for assisting realignment of a pelvis of a person according to claim 1, wherein said connection member has a first part connected to said first arm and a second part rotatably connected to said first part, said second arm being pivotably connected to said second part.

6. The method for utilizing an apparatus for assisting realignment of a pelvis of a person according to claim 5, wherein said connection member is substantial-ly spherical.

7. The method for utilizing an apparatus for assisting realignment of a pelvis of person according to claim 6, wherein said connection member is provided with a cut-out portion which accommodates an end of said first arm.

8. The method for utilizing an apparatus for assisting realignment of a pelvis of a person according to claim 1, wherein one of said first arm and said second arm is profiled for providing an upper protuberance for enabling said connection member to be gripped.

9. The method for utilizing an apparatus for assisting realignment of a pelvis of a person according to claim 1, wherein said first arm is provided with a recessed surface located on a side of said first arm remote from said second arm.

10. The method for utilizing an apparatus for assisting realignment of a pelvis of a person according to claim 9, wherein said first arm with the recessed surface is provided with rubber footings.

11. The method for utilizing an apparatus for assisting realignment of a pelvis of a person according to claim 1, wherein said second arm is provided with a recessed surface located on a side of said second arm remote from said first arm.

12. The method for utilizing an apparatus for assisting realignment of a pelvis of a person according to claim 9, wherein said second arm with the recessed surface is provided with rubber footings.

* * * * *